(12) United States Patent
Kisacanin et al.

(10) Patent No.: US 6,989,754 B2
(45) Date of Patent: Jan. 24, 2006

(54) TARGET AWARENESS DETERMINATION SYSTEM AND METHOD

(75) Inventors: Branislav Kisacanin, Kokomo, IN (US); Timothy J. Newman, Noblesville, IN (US); Gregory K. Scharenbroch, Kokomo, IN (US); Matthew R. Smith, Kokomo, IN (US); Gerald J. Witt, Carmel, IN (US); Glenn R Widmann, West Bloomfield, MI (US)

(73) Assignee: Delphi Technologies, Inc., Troy, MI (US)

( * ) Notice: Subject to any disclaimer, the term of this patent is extended or adjusted under 35 U.S.C. 154(b) by 1 day.

(21) Appl. No.: 10/452,756

(22) Filed: Jun. 2, 2003

(65) Prior Publication Data

US 2004/0239509 A1    Dec. 2, 2004

(51) Int. Cl.
*G08B 23/00* (2006.01)

(52) U.S. Cl. ...................... 340/576; 340/435; 340/436; 340/575; 340/539.25; 382/103

(58) Field of Classification Search ................ 340/435, 340/436, 539.25, 576; 180/274; 382/103; 701/301
See application file for complete search history.

(56) References Cited

U.S. PATENT DOCUMENTS

| | | | |
|---|---|---|---|
| 5,521,580 A * | 5/1996 | Kaneko et al. | 340/439 |
| 6,002,974 A | 12/1999 | Schiffmann | 701/36 |
| 6,496,117 B2 * | 12/2002 | Gutta et al. | 340/576 |
| 2003/0039378 A1 * | 2/2003 | Yuasa et al. | 382/104 |
| 2004/0178890 A1 * | 9/2004 | Williams et al. | 340/425.5 |

FOREIGN PATENT DOCUMENTS

| | | |
|---|---|---|
| DE | 43 38 244 | 5/1994 |
| DE | 197 34 307 | 2/1999 |
| DE | 101 35 742 | 2/2003 |

OTHER PUBLICATIONS

The American Heritage Dictionary of the English Language, Fourth Edition, 2000: Definitions of Radar, Lidar and Vector.*
European Search Report dated Jul. 29, 2004.

* cited by examiner

*Primary Examiner*—Jeffery Hofsass
*Assistant Examiner*—Anne V. Lai
(74) *Attorney, Agent, or Firm*—Stefan V. Chmielewski

(57) ABSTRACT

An object awareness determination system and method of determining awareness of a driver of a vehicle to an object is provided. The system includes an object monitor including an object detection sensor for sensing an object in a field of view and determining a position of the object. The system also includes an eye gaze monitor including an imaging camera oriented to capture images of the vehicle driver including an eye of the driver. The gaze monitor determines an eye gaze vector. The system further has a controller for determining driver awareness of the object based on the detected object position and the eye gaze vector.

20 Claims, 10 Drawing Sheets

TARGET AWARENESS DETERMINATION SYSTEM AND METHOD

TECHNICAL FIELD

The present invention generally relates to systems, such as collision warning and avoidance systems, for detecting objects and, more particularly, relates to a system and method of determining driver awareness of an object.

BACKGROUND OF THE INVENTION

Automotive vehicles are increasingly being equipped with collision avoidance and warning systems for predicting a high probability collision event with an object, such as another vehicle or a pedestrian. Upon detecting a potential collision event, such systems typically initiate safety-related countermeasure actions to avoid the collision and/or provide a warning to the vehicle operator. The ability to accurately predict a potential upcoming collision also enables a vehicle controller to evoke an appropriate safety-related countermeasure, such as initiate an avoidance chassis action (e.g., steer, brake and/or throttle) and/or deploy safety-related devices and/or deploy a warning signal to notify the vehicle operator of a predicted collision with an object.

Video image tracking systems have also been proposed for use on vehicles for tracking the face, including the eyes, of the driver to allow for determination of various facial characteristics of the driver including position, orientation, and movement of the driver's eyes, face, and head. By knowing the driver's facial characteristics, such as the driver's eye gaze, ocular data, head position, and other characteristics, vehicle control systems can provide enhanced vehicle functions. For example, vehicle control systems can advise the driver of driver distraction, driver inattention, or other drowsy driver situations.

Conventional collision warning/avoidance systems are generally considered an integration of an object tracking system comprised of an active detection sensor, such as a radar or lidar, in order to detect objects and provide estimates of their kinematic parameters (e.g., range, speed, and angle), and a threat determination and response system to assess a level of threat and determine the composition of safety-related countermeasures to be present to the driver. The response time initiation and composition of the appropriate safety-related countermeasure is highly dependent on the situational awareness of the driver. As such, in such a system implementation, there may exist errors in when the warning is provided and providing a warning level that is appropriate to the situational awareness of thedriver of the vehicle. When the driver is attentive, conventional collision warning systems may be perceived to provide excessive false warnings/alarms which may result in the driver disregarding warnings that are given. Contrarily, any resultant delays in reaction caused by driver unawareness of an associated risk may put the driver and other vehicle passengers at greater risk.

Accordingly, it is desirable to provide for a system that can determine the awareness of the driver to the surrounding environment and can enhance the performance delivered with a collision warning system. In particular, it is desirable to provide for an integrated system that minimizes false warnings/alarms that may be provided to a driver, particularly for use in a vehicle collision warning system.

SUMMARY OF THE INVENTION

The present invention provides for an object awareness determination system and method of determining awareness of a user to an object. According to one embodiment, the system determines awareness of the driver of a vehicle to a detected object. The system includes an object monitor having an object detection sensor for sensing an object in a field of view and determining a position of the object. The system also includes an eye gaze monitor having an imaging camera oriented to capture images of a user, including an eye of the user. The eye gaze monitor determines an eye gaze vector. The system further includes a controller for determining awareness of the user of an object based on the detected object position and the eye gaze vector.

The method of determining user awareness of an object includes the steps of sensing the presence of an object in a field of view, and determining a position of the object within the field of view. The method also includes the steps of monitoring eye gaze of a user, determining a gaze vector, and determining user awareness of the object as a function of the position of the object and the gaze vector.

Accordingly, the driver awareness determination system and method of the present invention advantageously integrates the eye gaze monitor and the object monitor to ensure that the driver is aware of target objects.

Thereby, the proposed invention allows the integration of a driver awareness determination systems, object tracking system, and threat assessment and response system such that an adaptive situational tailored safety-related countermeasure response is generated. As such, in the determination of a high potential collision event, the response time initiation and composition of the appropriate safety-related countermeasure is adaptively determined dependent on the situational awareness of the driver. This advantageously allows for the reduction of excessive false alarms which may otherwise occur in a conventional collision warning system.

These and other features, advantages and objects of the present invention will be further understood and appreciated by those skilled in the art by reference to the following specification, claims and appended drawings.

BRIEF DESCRIPTION OF THE DRAWINGS

The present invention will now be described, by way of example, with reference to the accompanying drawings, in which.

DESCRIPTION OF THE PREFERRED EMBODIMENTS

Figure 1:
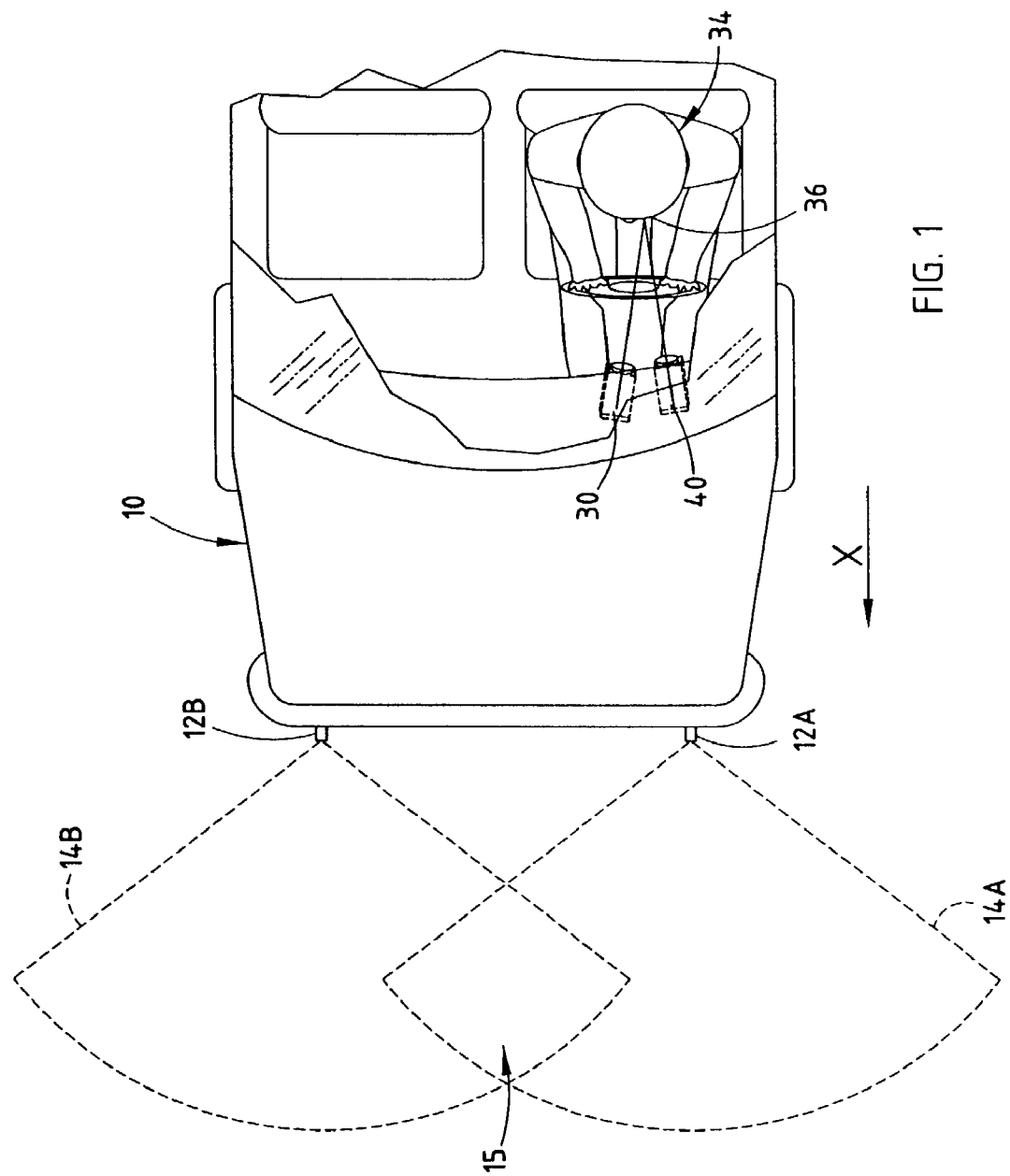
FIG. 1 is a plan view of a vehicle illustrating the geometry of sensor arrangements for a driver awareness determination system according to the present invention.

Referring to FIG. 1, an automotive vehicle 10 is generally illustrated having a target awareness determination system which integrates an object tracking monitor and an eye gaze monitor. The target awareness detection system monitors the position of an object as determined by the object tracking monitor, and further monitors the gaze vector of a driver 34 of the vehicle 10. The driver awareness determination system further determines if the driver 34 is aware of the object as a function of the object location and the eye gaze vector. By knowing whether or not the driver 34 is aware of the object, the target awareness determination system can advantageously be used to adaptively modify warning parameters in a collision warning system or other countermeasure system.

The target awareness determination system is shown and described herein in connection with a radar-based object tracking monitor (also referred to herein as an object tracking system) similar to that disclosed in U.S. application Ser. No. 10/196,631 and a dual-camera eye gaze monitor (also referred to herein as gaze monitor system) having a camera arrangement similar to that disclosed in U.S. application Ser. No. 10/103,202. However, it should be appreciated that other object tracking systems and eye gaze monitor systems could be employed in connection with the present invention.

The object tracking system is useful for detecting and tracking one or more objects, and may be further useful for predicting the potential collision of the object(s) with the host vehicle 10. The ability to predict the potential collision between the vehicle and an object using an object tracking system can be achieved by a variety of methods using either single or multiple active detection sensors, such as lidar, radar, or vision.

One such single sensor object tracking system implementation approach, uses a single narrow beamwidth radar and/or lidar signal that is mechanically swept over a large field of view. Within the sensor coverage field, the object tracking system has the ability to detect and track one or more stationary and/or non-stationary objects. Additionally, for each sensed object, the system provides the estimates of the velocity and relative position (e.g., range and angle), and assesses whether this object is in path with the host vehicle.

Another such implementation of an object tracking system includes a plurality of overlapping radar sensors 12A and 12B mounted to the vehicle 10 to cover a desired field of view, shown in front of the vehicle 10. According to the embodiment shown, the object tracking system has two radar sensors 12A and 12B located on opposite corners of the front of the vehicle 10. Radar sensor 12A detects objects within a first field of view 14A, and radar sensor 12B detects objects within a second field of view 14B. The radar sensors 12A and 12B are arranged so that the first and second fields of view 14A and 14B partially overlap to provide an overlapping coverage zone 15. The fields of view 14A and 14B also have non-overlapping regions.

The object tracking system senses and tracks one or more objects, such as a moving target, and estimates the position and velocity of the sensed target object, relative to the host vehicle 10. By estimating the current position and velocity of the target object within the overlapping coverage zone 15, the host vehicle 10 is able to track the object moving through the overlapping coverage zone 15 as well as through non-overlapping fields of view. It should be appreciated that the estimated position and velocity may be useful in tracking an object for purposes of determining collision detection and avoidance, such that responsive action may be taken to avoid a collision or to minimize the effects of a collision.

The eye gaze monitor system is shown employing a pair of video imaging cameras 30 and 40 focused on the face of the driver 34 of the vehicle 10. The first and second video cameras 30 and 40 may be integrated within the instrument cluster, within the steering column, within the dashboard, or at other locations within the vehicle 10 which allow for the acquisition of facial characteristics of the driver 34 including one or two eyes 36. The video cameras 30 and 40 are mounted such that each camera captures an image of the region where the driver 34 of the vehicle 10 is expected to be located during normal vehicle driving. More particularly, the images capture the driver's face, including one or both eyes 36 and the surrounding ocular features generally formed in the area referred to as the ocular adnexa.

Figure 2:
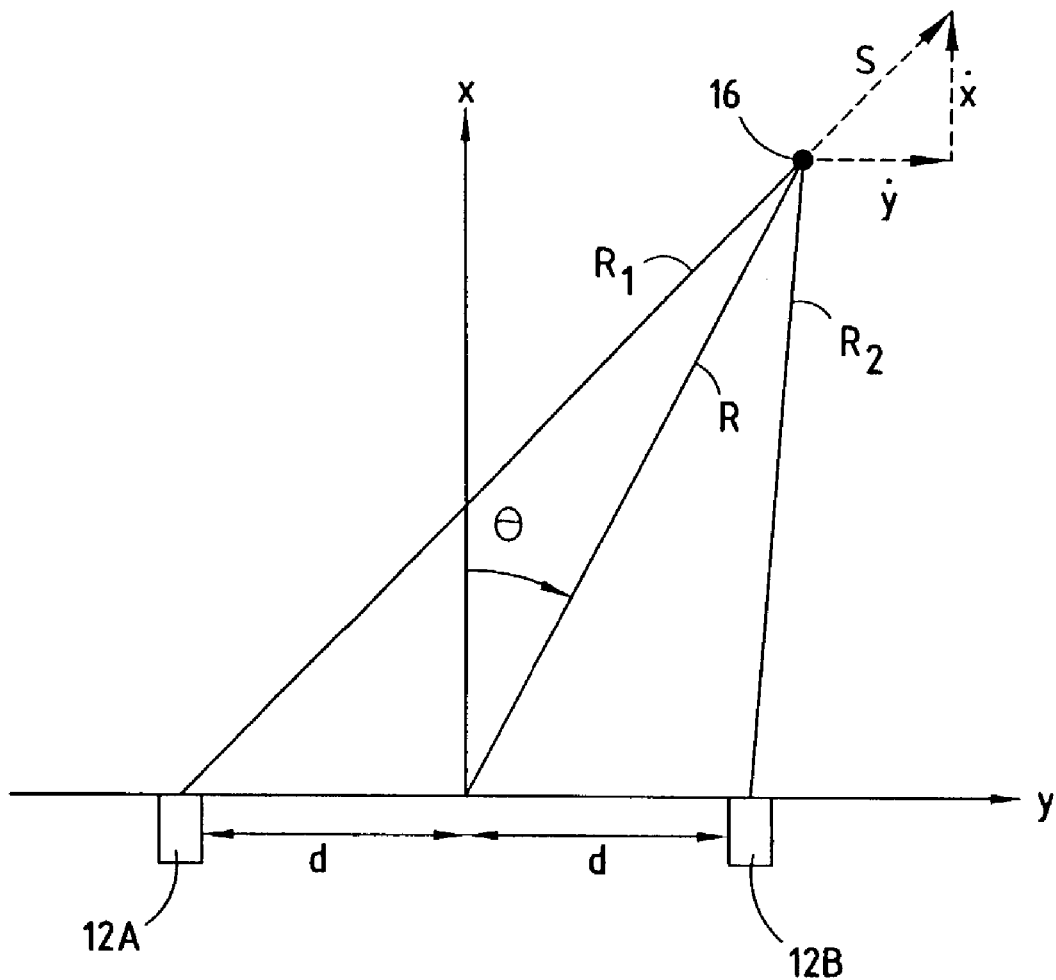
FIG. 2 is a plan view further illustrating the geometry of an object tracking system for tracking a target object.

The object tracking sensor arrangement shown includes a pair of sensors 12A and 12B arranged to define overlapping and non-overlapping coverage zones to sense the presence of one or more objects. Each of sensors 12A and 12B tracks the relative movement of each sensed object within fields of view 14A and 14B. Each of sensors 12A and 12B measures the range (radial distance) R1 and R2, respectively, as shown in FIG. 2, to a target object 16, measures the range rate (time rate of change of radial distance) R1 and R2 of target object 16, and further measures the received return radar signal amplitude A. The range R is the estimated radial distance between the host vehicle 10 and the object 16, and R1 and R2 represent the sensed range from sensors 12A and 12B, respectively. The range rate R is the estimated rate of change of the range R of the object 16 as a function of time relative to the host vehicle 10. The signal amplitude A is the amplitude of the reflected and returned radar signal received at each sensor.

Sensors 12A and 12B may each be a Doppler radar sensor that determines range rate k based on the radar Doppler effect. Sensors 12A and 12B may each include a commercially available off-the-shelf wide-beam staring microwave Doppler radar sensor. However, it should be appreciated that other object detecting sensors including other types of radar sensors, video imaging cameras, and laser sensors may be employed to detect the presence of an object, track the relative movement of the detected object, and determine the range and range rate measurements R and R and signal amplitudes A which, in turn, are processed to estimate the position and velocity of the target object 16.

The object tracking system described herein determines the position and velocity of the target object 16 as a function of the range R, range rate R, and signal amplitude A received at sensors 12A and 12B, without the requirement of acquiring an angular azimuth measurement of the object 16. Thus, the target tracking system is able to use a reduced complexity and less costly sensing arrangement. While a pair of sensors 12A and 12B are shown, it should be appreciated that any number of sensors may be employed and may provide multiple overlapping fields of view (overlapping coverage zones). The radar sensor coverage zones may extend in front, behind or towards the sides of the vehicle 10.

The tracking system estimates the position and velocity of the target object 16 when the object 16 is in the overlapping coverage zone 15 sensed by multiple sensors, and continues to track the object 16 as it moves through the overlapping coverage zone 15 and non-overlapping zones within the first and second fields of view 14A and 14B. When the target object 16 is in the overlapping coverage zone 15, an extended Kalman filter is employed to estimate the position and velocity of the object 16 using range and range rate triangulation and a signal amplitude ratio $A_R$. When the object 16 is outside of the overlapping coverage zone 15, but remains within one of the first and second fields of view 14A and 14B, the object tracking system continues to track the object 16 by employing a single beam tracking algorithm using the current measurements and the last known position and velocity when in the overlapping coverage zone 15. This single beam tracking algorithm may estimate an azimuth angular rate using range and range rate measurements.

In order to track an object 16 in the overlapping coverage zone 15, the object 16 may be assumed to be a point reflector. As shown in FIG. 2, the sensors 12A and 12B are separated by a distance 2d which, in a vehicle application, is typically limited to the width of the vehicle 10. The angle θ may be determined as a function of the range and amplitude of the signals received by sensors 12A and 12B. The received amplitude measurements of sensors 12A and 12B are processed as follows. Using a point reflector move to varying locations in the overlapping coverage zone 15 of the two sensors 12A and 12B, and construct a lookup table which maps range R and amplitude ratio $A_R$ into azimuth angle of the object 16. Amplitude ratio $A_R$ refers to the ratio of the sensed amplitudes of the received signal returns from the two sensors 12A and 12b. A synthetic measurement (estimation) of azimuth angle may thus be constructed from the two amplitude measurements for a given target range. Synthetic measurements of position coordinates (x, y) are then constructed using the azimuth angle and the estimated range midway between sensors 12A and 12B. The synthetic measurements of position coordinates are compared to the current position estimates, and the filter state variables are updated accordingly. Thus, the range R, range rate R, and received signal amplitude A measurements from the two sensors 12A and 12B are used to measurement update the filter states.

Since the relationship between the state variables and the predicted measurements are not linear, a non-linear filter, preferably an extended Kalman filter, is used. It should be appreciated that other non-linear filters could be employed, such as an unscented Kalman filter or a particle filter. The measurement noise covariance matrix, which statistically describes the anticipated errors in the various measurements, is used to tune the filter response to range, range rate, and received signal amplitude measurements. The extended Kalman filter further provides a time update which describes how the state variables are believed to evolve in time. The state variables are two position coordinates x and y and two velocity components $\dot{x}$ and $\dot{y}$. The position states evolve in the usual linear way according to the corresponding velocities. The velocities are modeled as random walks which are roughly constant but change slowly. A process noise covariance matrix describes the levels of the uncertainties in the above model and, in particular, allows for tuning. Mathematical models of process dynamics and measurements are shown and described herein.

Figure 3:
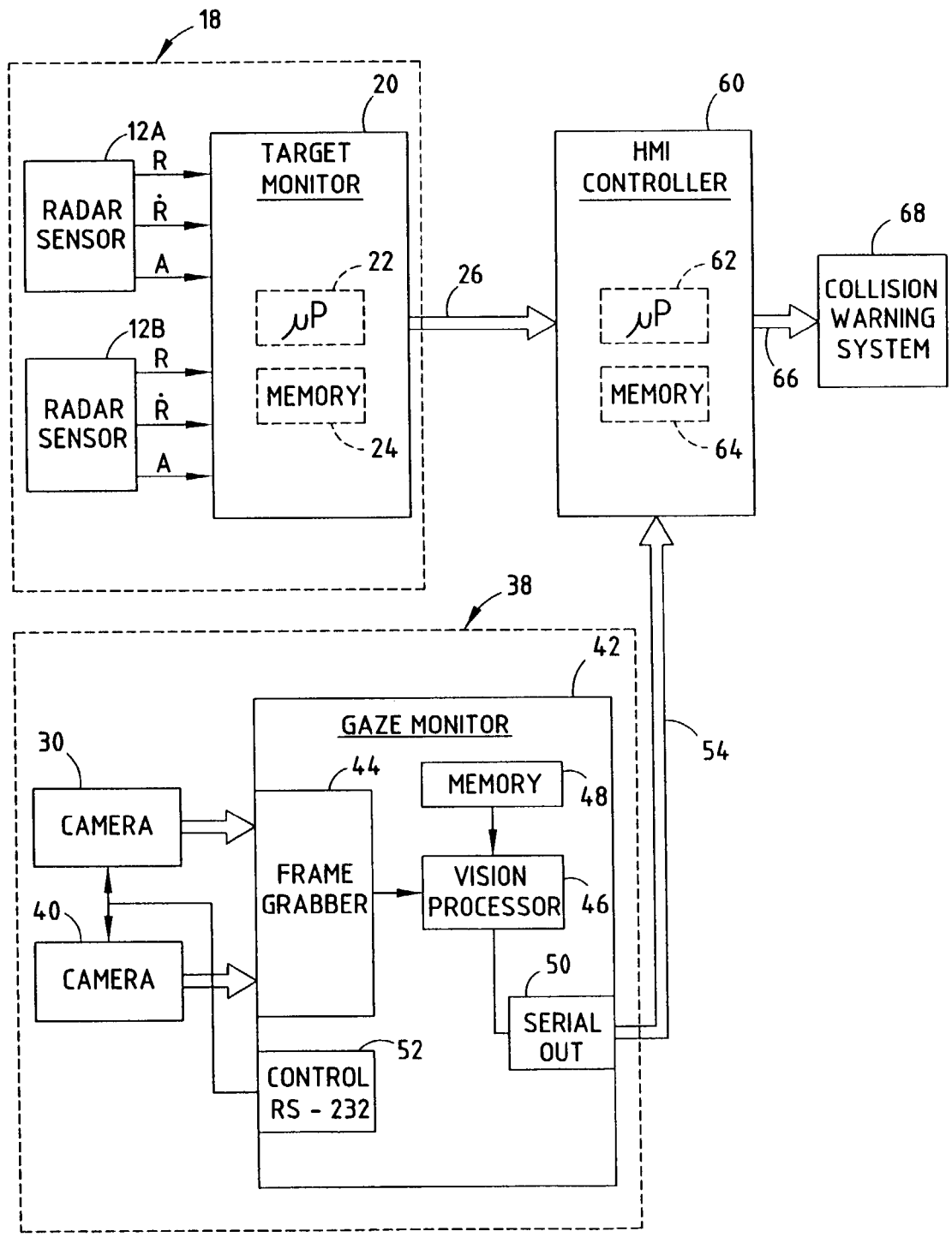
FIG. 3 is a block diagram illustrating the driver awareness determination system according to the present invention.

Referring to FIG. 3, the target awareness determination system is shown including the object tracking system 18, the eye gaze monitor system 38, and an HMI controller 60 for providing control output signals to a collision warning system 68. The HMI controller 60 processes the output signals 26 and 54 and determines a driver awareness condition according to the present invention. The HMI controller 60 further generates one or more outputs 66 which may be used to adjust parameters, such as thresholds, of the collision warning system 68.

The object tracking system 18 includes radar sensors 12A and 12B and a target monitor 20. Target monitor 20 preferably includes a microprocessor-based controller having a microprocessor 22 and memory 24. Memory 24 may include random access memory (RAM), read-only memory (ROM), electrically erasable programmable read-only memory (EEPROM), and other memory as should be evident to those skilled in the art. Target monitor 20 may be a commercially available off-the-shelf controller and may be dedicated to target tracking, adaptive cruise control or crash processing, according to some examples, or may share processing capability with other vehicle functions.

The target monitor 20 receives the range measurement R, range rate measurement R, and signal amplitude A from each of radar sensors 12A and 12B, and processes the received signals with one or more target tracking routines to determine the position and velocity of the target object 16 relative to the host vehicle 10. The target tracking routine(s) may further process the estimated position and velocity to determine whether a potential collision of the target object 16 with the host vehicle 10 may occur or to control some other vehicle function(s). The target monitor 20 generates output signals 26 that are made available to the HMI controller 60 and may be made available to various other systems.

The eye gaze monitor system 38 includes the first and second video cameras 30 and 40 coupled to a gaze monitor 42. Video cameras 30 and 40 may include CCD/CMOS active-pixel digital image sensors each mounted as individual chips onto a circuit board. One example of a CMOS active-pixel digital image sensor is Model No. PB-0330, commercially available from Photobit, which has a resolution of 640 H×480 V.

The gaze monitor 42 is shown having a frame grabber 44 for receiving the video frames generated by the first and second video cameras 30 and 40. The gaze monitor 42 includes a vision processor 46 for processing the video frames. The gaze monitor 42 also includes memory 48, such as RAM, ROM, EEPROM, and other memory as should be evident to those skilled in the art. The vision processor 46 may be configured to perform one or more routines for identifying and tracking one or more features in the acquired video images, and may be further configured to perform one or more vehicle functions based on the tracked information. For example, the eye gaze monitor system 38 may identify and track a facial characteristic of the driver 34, such as ocular motility or palpebral fissure, and determine a driver drowsy situation. According to another example, the eye gaze monitor system 38 may determine the presence of a distracted or inattentive driver. The gaze monitor 42 processes the video images containing the facial characteristics and determines an eye gaze vector g of one or more eyes 36 of the driver 34 of the vehicle 10, and generates output signals 54 via serial output 40, which are input to the HMI controller 60. In lieu of the frame grabber 44, it should be appreciated that the digital video may be input via video ports to vision processor 46, which may then store the images in memory 48.

Further, the gaze monitor 42 has a control function 52 via RS-232 which allows for control of each of the first and second cameras 30 and 40. Control of the first and second cameras 30 and 40 may include automatic adjustment of the pointing orientation of the first and second cameras 30 and 40. For example, the first and second cameras 30 and 40 may be repositioned to focus on an identifiable feature, and may scan a region in search of an identifying feature. Control may include adjustment of focus and magnification as may be necessary to track an identifiable feature. Thus, the eye gaze monitor system 38 may automatically locate and track an identifiable feature, such as the driver's eye 36 and other facial characteristics.

The HMI controller 60 includes a microprocessor-based controller having a microprocessor 62 and memory 64. Memory 64 may include RAM, ROM, EEPROM, and other memory as should be evident to those skilled in the art. The HMI controller 60 is programmed to include one or more routines for determining driver awareness of a target object 16 based on the position of the object 16 and the eye gaze vector $\bar{g}$. The HMI controller 60 further provides output signals 66 based on the determined driver awareness to a collision warning system 68 and possibly other systems. The collision warning system 68 may utilize the driver awareness output signals 66 to adjust parameters in the collision warning system 68 such as to provide different thresholds for a visual and/or audible warning to the driver 34 of the vehicle 10. For example, when the HMI controller 60 determines that the driver 34 is aware of an object 16, the collision warning system 68 may change threshold parameters so as to minimize the presence of excessive false alarms. While the target awareness determination system is described in connection with a target monitor 20, an eye gaze monitor 42, and an HMI controller 60, each having a microprocessor and memory, it should be appreciated that the target tracking, eye gaze monitoring, and driver awareness determination routines may be implemented in any one or more processors, without departing from the teachings of the present invention.

Figure 4:
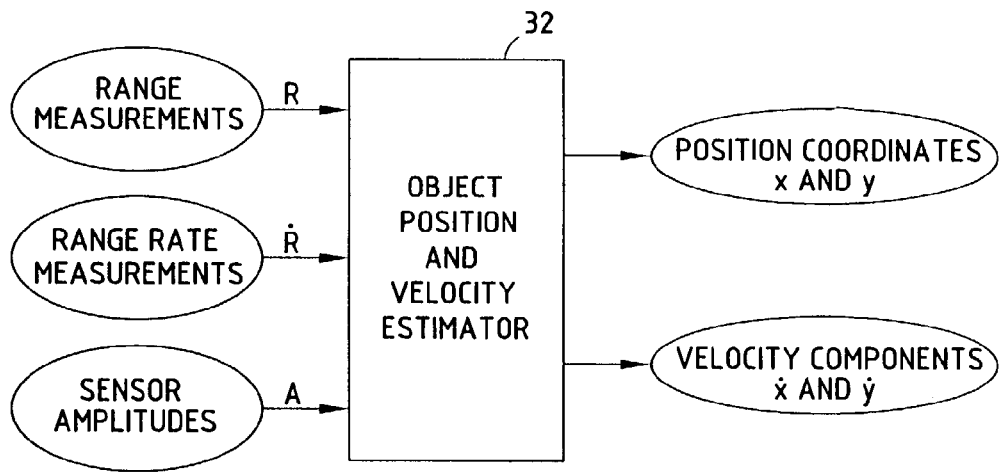
FIG. 4 is a block diagram illustrating an object position and velocity estimator of the object tracking system.
Figure 5:
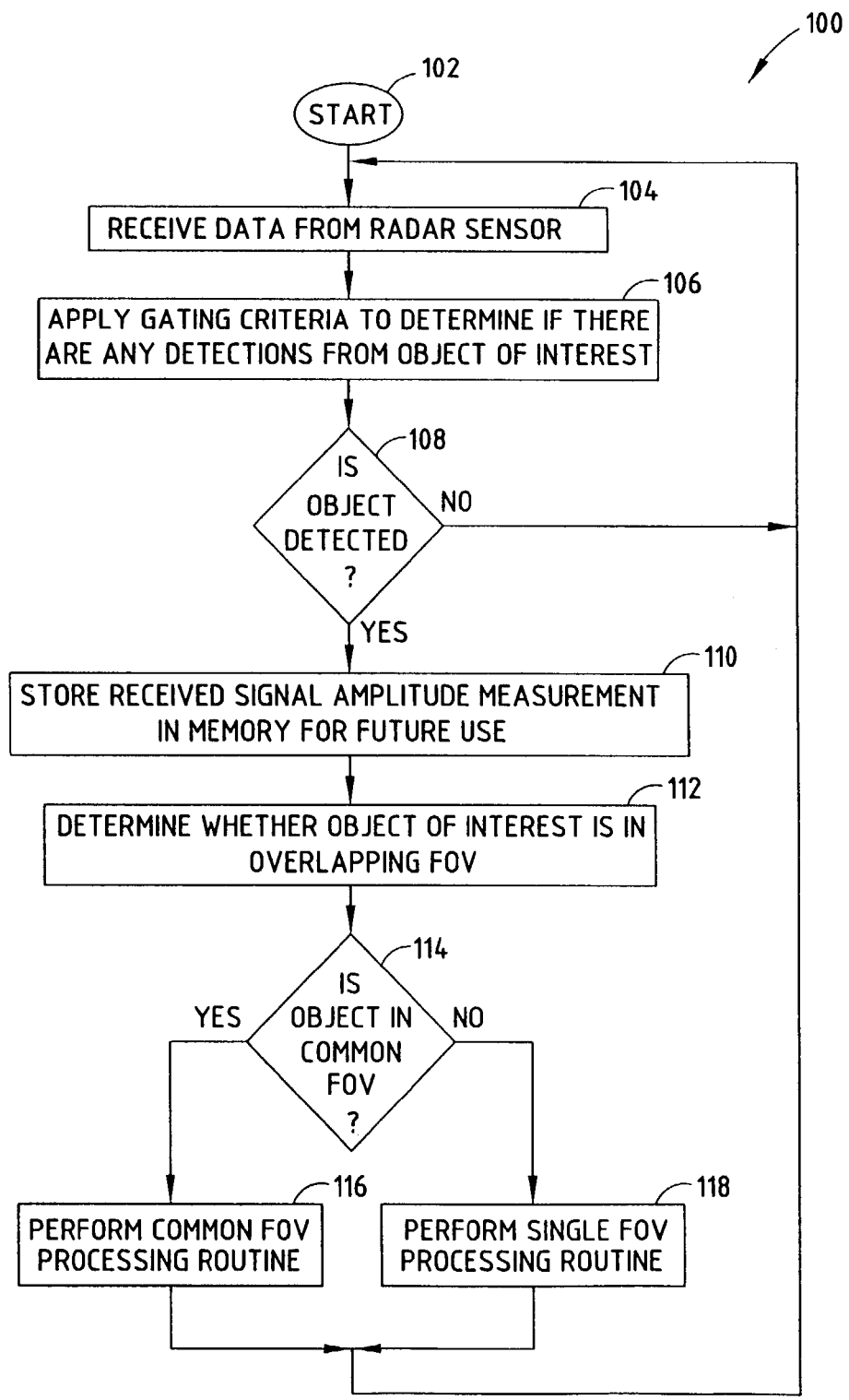
FIG. 5 is a flow diagram illustrating a routine for tracking an object according to the present invention.
Figure 6:
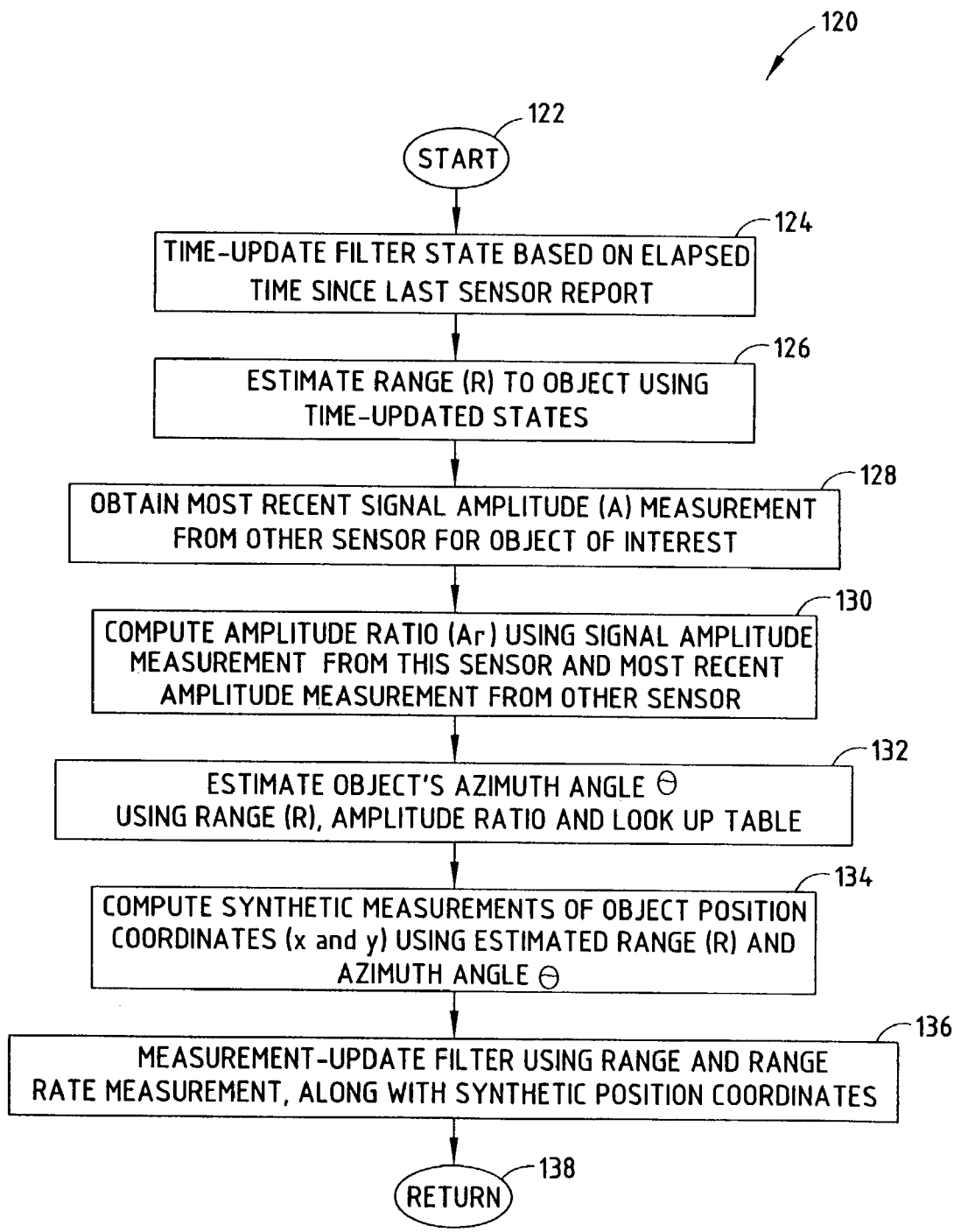
FIG. 6 is a flow diagram illustrating a routine for estimating object position and velocity when the object is in an overlapping coverage zone.
Figure 7:
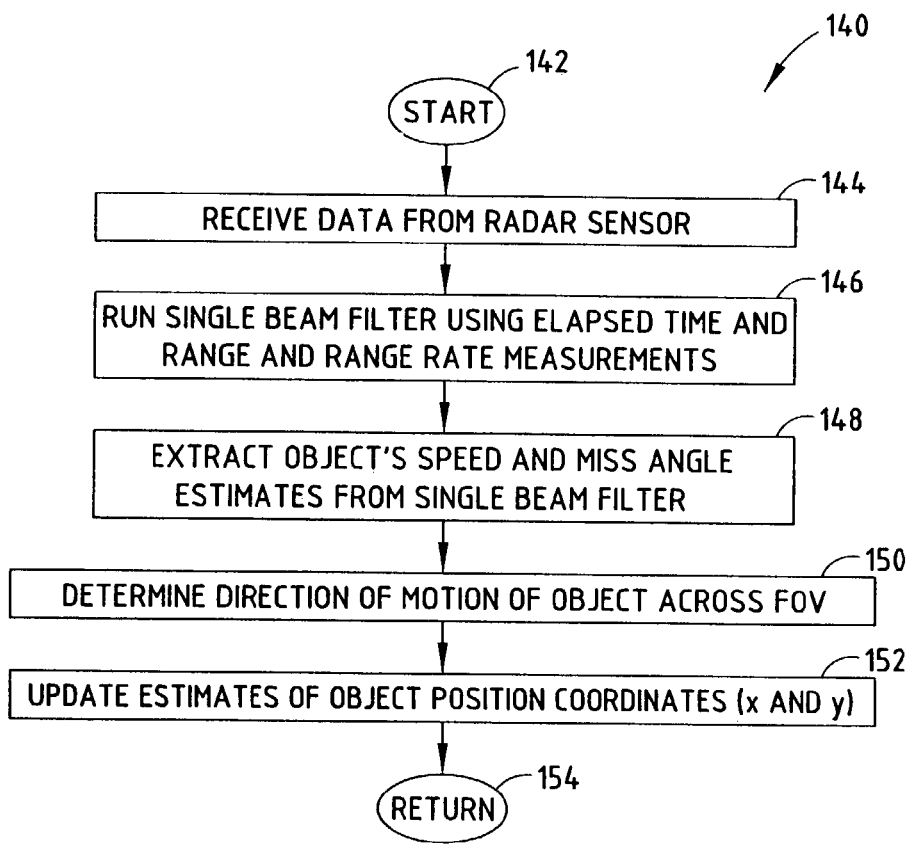
FIG. 7 is a flow diagram illustrating a routine for estimating object position and velocity when the object travels in a sensor field of view outside of the overlapping coverage zone.

Referring to FIG. 4, an object position and velocity estimator 32 is generally shown receiving the range measurements R, range rate measurements R, and amplitude measurements A from both of sensors 12A and 12B. The range R, range rate R, and amplitude A measurements are processed by the estimator 32, which includes programmed routines, as shown in FIGS. 5–7 and described in more detail below, to estimate the position and velocity of the target object 16.

When the target object 16 is located within the overlapping coverage zone 15, an extended Kalman filter is employed to estimate the object position coordinates x and y and to estimate the velocity components $\dot{x}$ and $\dot{y}$ of the object 16. The non-linear extended Kalman filter inputs a sequence of measurements and, at each measurement time k, k+1, k+2, etc., estimates of the target object attributes for position and velocity at the current time k are updated. The estimation problem for the non-linear extended Kalman filter is explained below with the filter state model, process dynamics model, and measurement model.

Filter State Model $$\bar{x} = \begin{bmatrix} x \\ \dot{x} \\ y \\ \dot{y} \end{bmatrix}$$

where x is the downrange position coordinate of target object, $\dot{x}$ is the downrange relative velocity component of target object, y is the crossrange position coordinate of target object, and $\dot{y}$ is the crossrange relative velocity component of target object.

Process Dynamics Model $$\bar{x}_{k+1} = F\bar{x}_k + \bar{w}_k$$

where $$F = \begin{bmatrix} 1 & T & 0 & 0 \\ 0 & 1 & 0 & 0 \\ 0 & 0 & 1 & T \\ 0 & 0 & 0 & 1 \end{bmatrix}$$

and $\bar{w}_k$ is a zero-mean random vector (process noise) having covariance $$Q = \begin{bmatrix} \frac{\sigma_x T^3}{3} & \frac{\sigma_x T^2}{2} & 0 & 0 \\ \frac{\sigma_x T^2}{2} & \sigma_x T & 0 & 0 \\ 0 & 0 & \frac{\sigma_y T^3}{3} & \frac{\sigma_y T^2}{2} \\ 0 & 0 & \frac{\sigma_y T^2}{2} & \sigma_y T \end{bmatrix}$$

wherein $\sigma_x, \sigma_y$ are calibrations, subscripts k and k+1 refer to discrete time instants, and T is the elapsed time between instants k and k+1.

Measurement Model

Sensor 12A:

$$R1 = \sqrt{x^2 + (y+d)^2} + v_1 \quad \text{(Range from sensor 12A)}$$

$$\dot{R1} = \frac{x\dot{x} + (y+d)\dot{y}}{\sqrt{x^2 + (y+d)^2}} + v_2 \quad \text{(Range rate form sensor 12A)}$$

$$R\cos\theta = x + v_3 \quad \text{(Synthetic measurement of downrange coordinate)}$$

$$R\sin\theta = y + v_4 \quad \text{(Synthetic measurement of crossrange coordinate)}$$

where R= $\sqrt{x^2+y^2}$ is the estimated range from the origin O of coordinates, θ is obtained from lookup table using estimated range R and amplitude ratio $A_R$ of two most recent signal amplitude measurements from sensors 12A and 12B, and v is a zero-mean random vector representing measurement errors having covariance as shown below.

$$\overline{v} = \begin{bmatrix} v_1 \\ v_2 \\ v_3 \\ v_4 \end{bmatrix}$$

Sensor 12B:

$R2 = \sqrt{x^2 + (y-d)^2} + v_1$ (Range from sensor 12B)

$\dot{R}2 = \dfrac{x\dot{x} + (y-d)\dot{y}}{\sqrt{x^2 + (y-d)^2}} + v_2$ (Range rate form sensor 12B)

$R\cos\theta = x + v_3$ (Synthetic measurement of downrange coordinate)

$R\sin\theta = y + v_4$ (Synthetic measurement of crossrange coordinate)

where $R = \sqrt{x^2 + y^2}$ is the estimated range from the origin O of coordinates, $\theta$ is obtained from lookup table using estimated range R and amplitude ratio $A_R$ of two most recent signal amplitude measurements from sensors 12A and 12B, and $\overline{v}$ is a zero-mean random vector representing measurement errors having covariance as shown below.

$$\overline{v} = \begin{bmatrix} v_1 \\ v_2 \\ v_3 \\ v_4 \end{bmatrix}$$

When the target object 16 leaves the overlapping coverage zone 15 and remains within one of the field of views 14A and 14B, the target object 16 may be further tracked based on the last known position and velocity estimations of the object 16. This may be accomplished by employing a single field of view tracking routine which may include one of the routines disclosed in either of pending U.S. application Ser. No. 10/158,550, filed on May 30, 2002, entitled "COLLISION DETECTION SYSTEM AND METHOD OF ESTIMATING MISS DISTANCE," and U.S. application Ser. No. 10/159,959, filed on May 30, 2002, entitled "COLLISION DETECTION SYSTEM AND METHOD OF ESTIMATING MISS DISTANCE EMPLOYING CURVE FITTING," the entire disclosures of which are hereby incorporated herein by reference. The techniques described in the aforementioned applications can determine the azimuth angular rate of a target object 16 using range and range rate measurements by estimating the range and speed of the object along with the magnitude of a miss angle which is the angle between the radar sensor to the object and the object's velocity vector. Given the last known position and velocity of the object 16 acquired in the overlapping coverage zone 15, the trajectory of the object 16 can be estimated until the object 16 leaves the fields of view 14A and 14B.

Referring to FIG. 5, a routine 100 is illustrated for estimating the position and velocity of the target object. Routine 100 begins at step 102 and proceeds to step 104 to receive the sensor measurement data from one of the radar sensors. Next, in step 106, the routine 100 applies gating criteria to determine if there is detection of an object of interest from the field of view of the radar sensor. In decision step 108, routine 100 determines if an object is detected by the radar sensor and, if not, returns to step 104. If an object is detected by the radar sensor, routine 100 proceeds to step 110 to store in memory the amplitude A measurement of the returned radar signal received by the radar sensor. Next, routine 100 determines whether the object of interest is in an overlapping field of view (FOV) coverage zone for multiple radar sensors in step 112. In decision step 114, routine 100 decides which processing routine is performed based on whether the object detected is determined to be within the overlapping FOV coverage zone. If the object detected is within an overlapping FOV coverage zone, routine 100 proceeds to step 116 to perform a common FOV processing routine, as described in connection with FIG. 6, before returning to the beginning of routine 100. If the object detected is not within the overlapping coverage zone, routine 100 proceeds to perform a single FOV processing routine in step 118, which is shown in FIG. 7, before returning to the beginning of routine 100. Routine 100 is repeated each loop so that new data from one of sensors 12A and 12B is introduced during one loop and the new data from the other sensors 12A and 12B is introduced during the next loop.

Referring to FIG. 6, the common field of view processing routine 120 is shown beginning at step 122 and proceeding to step 124 to time-update the extended Kalman filter state based on an elapsed time since the last sensor report. Next, in step 126, routine 120 estimates the range R to the object using the time-updated states. Routine 120 then obtains the most recent signal amplitude A measurements from the other sensor for the same object of interest in step 128.

In step 130, common FOV processing routine 120 computes the amplitude ratio $A_R$ using amplitude measurements A from the current sensor and the most recent amplitude measurement A from the other sensor for the same object of interest. Thus, the amplitude ratio $A_R$ is based on the most recently acquired data. In step 132, routine 120 estimates the azimuth angle $\theta$ of the object using range R, the amplitude ratio $A_R$, and a lookup table. Proceeding to step 134, routine 120 computes synthetic measurements (estimations) of object position coordinates x and y using the estimated range R and azimuth angle $\theta$. Finally, in step 136, routine 120 measurement-updates the filter using range R and range rate R measurements along with the synthetic position coordinates x and y before returning in step 138.

Accordingly, the common field of view processing routine 120 estimates the position coordinates x and y and velocity components $\dot{x}$ and $\dot{y}$ of an object 16 by employing an extended Kalman filter based on the sensed range R, range rate R, and signal amplitude A measurements acquired from at least two radar sensors when the target object 16 is within the overlapping coverage zone 15. When the target object 16 leaves the overlapping coverage zone 15 and remains within one of the non-overlapping fields of view 14A and 14B, the single field of view processing routine 140 may be performed as shown in FIG. 7.

Referring to FIG. 7, single FOV processing routine 140 starts at step 142 and proceeds to step 144 to receive sensor measurement data from a radar sensor. Next, in step 146, routine 140 runs a single beam filter using the elapsed time and range R and range rate R measurements as acquired from the appropriate radar sensor covering the single FOV of interest. Routine 140 then extracts the object's speed and miss angle estimates from the single beam filter in step 148 and determines direction of motion of the object across the field of view in step 150. Finally, in step 152, routine 140 updates the estimates of object position coordinates x and y before returning in step 154.

Figure 8:
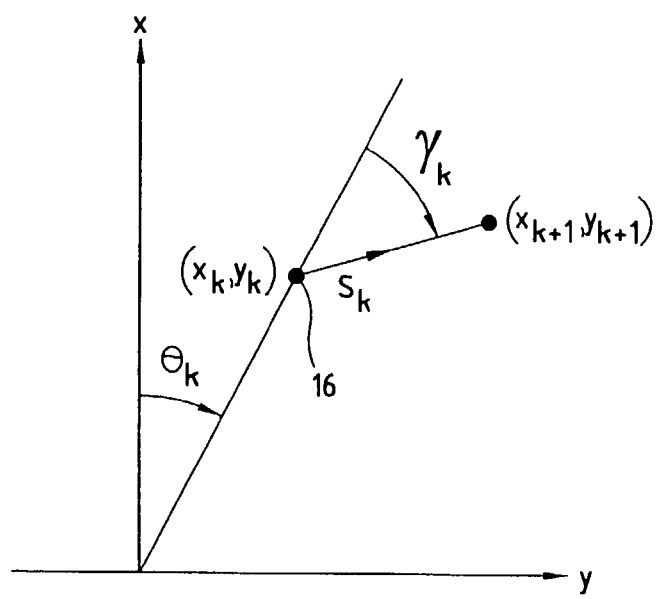
FIG. 8 is a plan view further illustrating the geometry of tracking the object in a single field of view.

An example of the geometry for tracking an object 16 in a non-overlapping field of view with a single field of view tracking algorithm is shown in FIG. 8. The target 16 is shown at different time periods k and k+1. At time period k, object 16 has position coordinates $x_k$ and $y_k$. As the object 16 travels during an elapsed time period, object 16 has time-updated position coordinates $x_{k+1}$ and $y_{k+1}$. The object 16 has a magnitude of target velocity vector $S_k$ and the target object has a miss angle at time k of $\gamma_k$. The single field of view processing algorithm is able to update the position coordinates x and y of the object based on the object speed $S_k$ and miss angle $\gamma_k$ estimates for each consecutive time period increment.

It should be appreciated that the single field of view processing routine 140 may employ any of a number of algorithms for tracking a target object through a single field of view of a sensor once the position and velocity of the object are obtained. Examples of single field of view processing techniques are disclosed in pending U.S. application Ser. Nos. 10/158,550 and 10/159,959, both filed on May 30, 2002.

It should be appreciated that the extended Kalman filter may be designed and implemented to estimate the position and velocity of the target object 16 by employing the state variables, the process model, and the measurement model as described above. In addition, standard models of process and measurement noise could be employed. The extended Kalman filter may be implemented in various forms such as a smoother or a non-linear filter which is based on the selection of physical quantities to be represented by state variables in the filter, the dynamic models chosen to represent the interaction and time-evolution of the state variables, and the measurement model chosen to represent how the available measurements are related to the values taken by the physical quantities represented in the state variables. The extended Kalman filter handles non-linearities in the models, particularly in the measurement model. It should be appreciated that extended Kalman filters have been employed in automotive applications such as vehicle rollover sensing as disclosed in U.S. Pat. No. 6,002,974, entitled "VEHICLE ROLLOVER SENSING USING EXTENDED KALMAN FILTER," the disclosure of which is hereby incorporated herein by reference.

Figure 9:
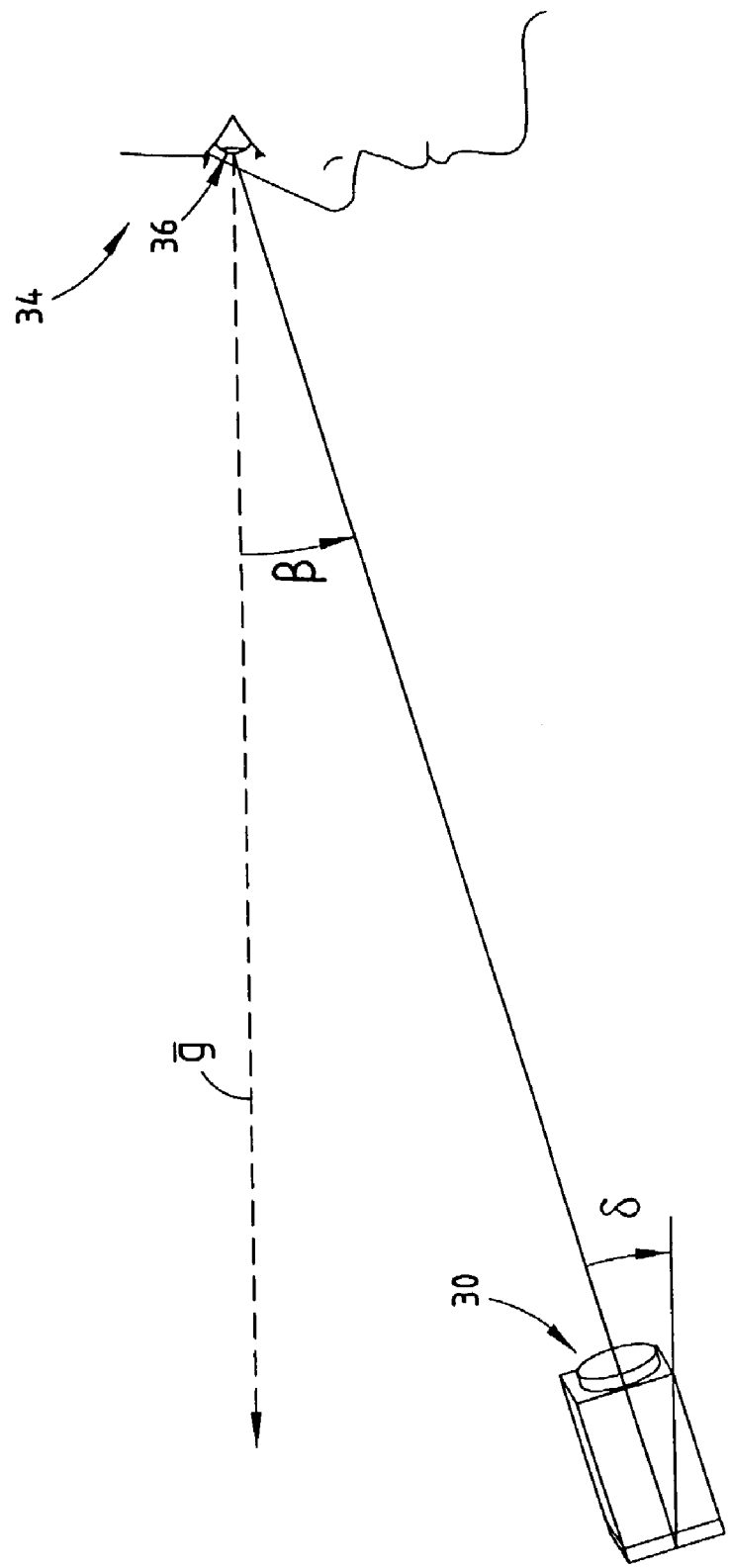
FIG. 9 is a side perspective view of the projection of one of the video cameras towards the face of the driver.

Referring to FIG. 9, the first camera 30 is shown focused at an inclination angle β relative to the horizontal plane of the vehicle 10. The inclination angle β is within a range of fifteen to thirty degrees (15° to 30°). An inclination angle β in the range of fifteen to thirty degrees (15° to 30°) provides a clear view of the driver's ocular features including one or both eyeballs 36 and the pupil of the eyeballs, the superior and inferior eyelids, and the palpebral fissure space between the eyelids. The second camera 40 is similarly mounted at the same or similar inclination angle β. Also shown is a gaze vector $\bar{g}$ which is the line-of-sight vector of the eyeball 36 of the driver 34. The gaze vector $\bar{g}$ is the vector at which the eye 36 is focused and is indicative of the line-of-sight direction that the driver 34 of the vehicle 10 realizes.

Figure 10:
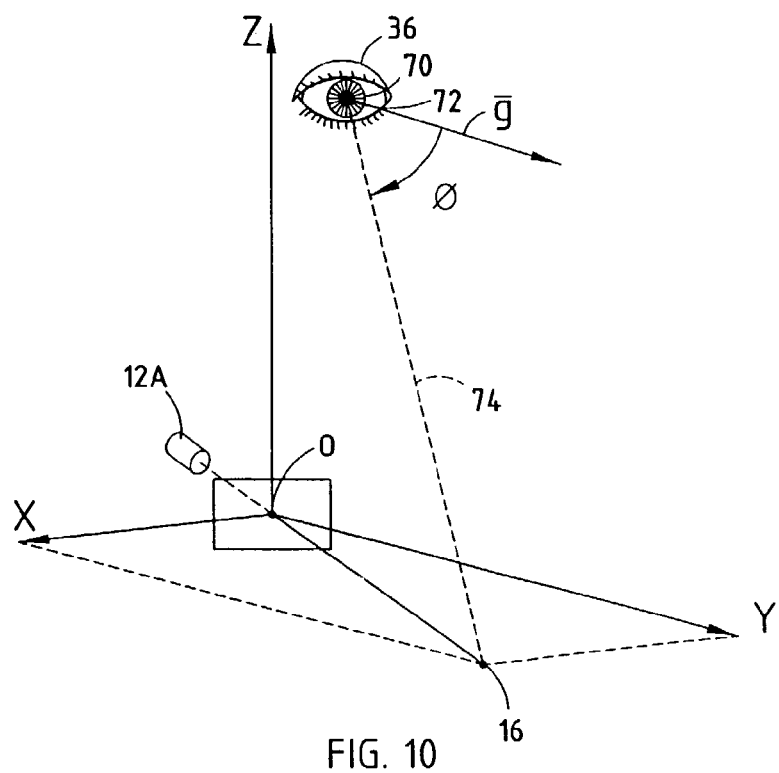
FIG. 10 is a plan view illustrating the geometry for determining an awareness angle.

The target awareness determination system of the present invention determines an awareness angle φ which is shown in FIG. 10. The awareness angle φ is the angle between the gaze vector $\bar{g}$ and a line 74 extending from the driver's eye 36 to the target object 16. The awareness angle φ serves as an indication of whether the driver 34 is visually aware of the target object 16. The target awareness determination system uses a recent history of the awareness angle φ to infer the driver's awareness of the target object 16. The eye gaze monitor system 38 determines (e.g., estimates) the driver's head position $\bar{h}$ in three dimensions (x, y, z) as well as three-dimensional coordinates of the gaze vector $\bar{g}$. The three-dimensional coordinates of the gaze vector $\bar{g}$ may be represented as $\bar{g}=(g_x, g_y, g_z)$. The eye gaze vector $\bar{g}$ is processed in combination with the three-dimensional information about the target object 16 provided by the object tracking system 18 to determine the driver awareness.

The origin O is the location either at radar sensor 12A or 12B or is a middle location between sensors 12A and 12B that serves as the average sensor location. The object tracking system outputs the three-dimensional location of the object target 16 represented by target coordinates $\bar{t}=(t_x, t_y, t_z)$. The coordinates of the driver's head $\bar{h}$ in this reference system depend on the relative position of the driver's head with respect to the eye gaze monitor system 38 (which is an output of the eye gaze monitor system 38) and the relative position of the gaze monitor system with respect to the origin O (which is a known vehicle parameter). Hence, the three-dimensional coordinates of the driver's head may be represented as $\bar{h}=(h_x, h_y, h_z)$. Given the gaze vector $\bar{g}$, head coordinates $\bar{h}$ and target coordinates $\bar{t}$, the awareness angle φ can be determined from the following formula:

$$\cos\phi = \frac{(\bar{t}-\bar{h})\cdot \bar{g}}{|\bar{t}-\bar{h}|\cdot|\bar{g}|} = \frac{(t_x-h_x)g_x + (t_y-h_y)g_y + (t_z-h_z)g}{\sqrt{(t_x-h_x)^2+(t_y-h_y)^2+(t_z-h_z)^2}\sqrt{g_x^2+g_y^2+g_z^2}}$$

The target awareness determination system monitors the awareness angle φ and, if the awareness angle φ is not less than a predetermined angle of about two degrees (2°) for a minimum time period from the moment the object tracking system detects a new threat-posing or information-caring target object, the system assumes that the driver did not perceive the target object as a threat or new information. The predetermined angular threshold of two degrees (2°) is similar to the angular width of the fovea, which is a central area of the retina of the eye 36. In a typical eye-scanning behavior, the driver 34 will immediately foveate the target object 16 when the driver 34 notices the threat developing in the driver's peripheral vision. In doing so, the eye 36 will refocus to the target object such that the awareness angle φ does not exceed the predetermined angle of about two degrees (2°). Furthermore, if the awareness angle φ is less than the predetermined angle for a very short time less than the minimum time period of thirty milliseconds (30 ms), according to one embodiment, which may occur in one video frame, the system does not conclude that the driver 34 has perceived the threat of the object 16, because the driver 34 could be coincidentally saccading across the target object 16 without noticing the object 16. Thus, the target awareness determination system of the present invention employs a recent time history of the awareness angle φ to insure that the awareness angle φ is less than about two degrees (2°) for a minimum time period of at least thirty milliseconds (30 ms) before making a determination that the driver 34 is aware of the target object 16.

The knowledge of whether or not the driver 34 is aware of the target object 16 is useful to adaptively modify the warning parameters of a warning system, such as a collision warning system. For example, the driver 34 might be monitoring a lateral target while momentarily neglecting a forward target. During this time, if the lateral target is a vehicle that begins braking, a side collision warning system could be suppressed or delayed. However, if the forward visual target that is not being attended to is a vehicle that initiates a braking maneuver, the forward collision warning could be presented immediately. Adaptively shifting warning thresholds based on the driver awareness determination realized with the awareness angle φ will serve to reduce the frequency of nuisance alarms and will further provide useful warnings earlier to the driver 34.

Many forward collision warning systems use one or more levels of warning(s). For example, a forward collision warning system may include both cautionary and imminent warning levels. The imminent warning level(s) is generally accompanied by an auditory stimulus, but, in order to reduce driver annoyance, the cautionary level may use only a visual stimulus. Because an auditory stimulus is useful for reorienting an inattentive driver to the relevant target object, the cautionary level could be accompanied with an auditory stimulus when the driver 34 is not attending to the relevant target. Because the warnings would only alert the driver 34 when the driver 34 is unaware of the developing threat, this decreases false alarms which reduces driver annoyance.

Figure 11:
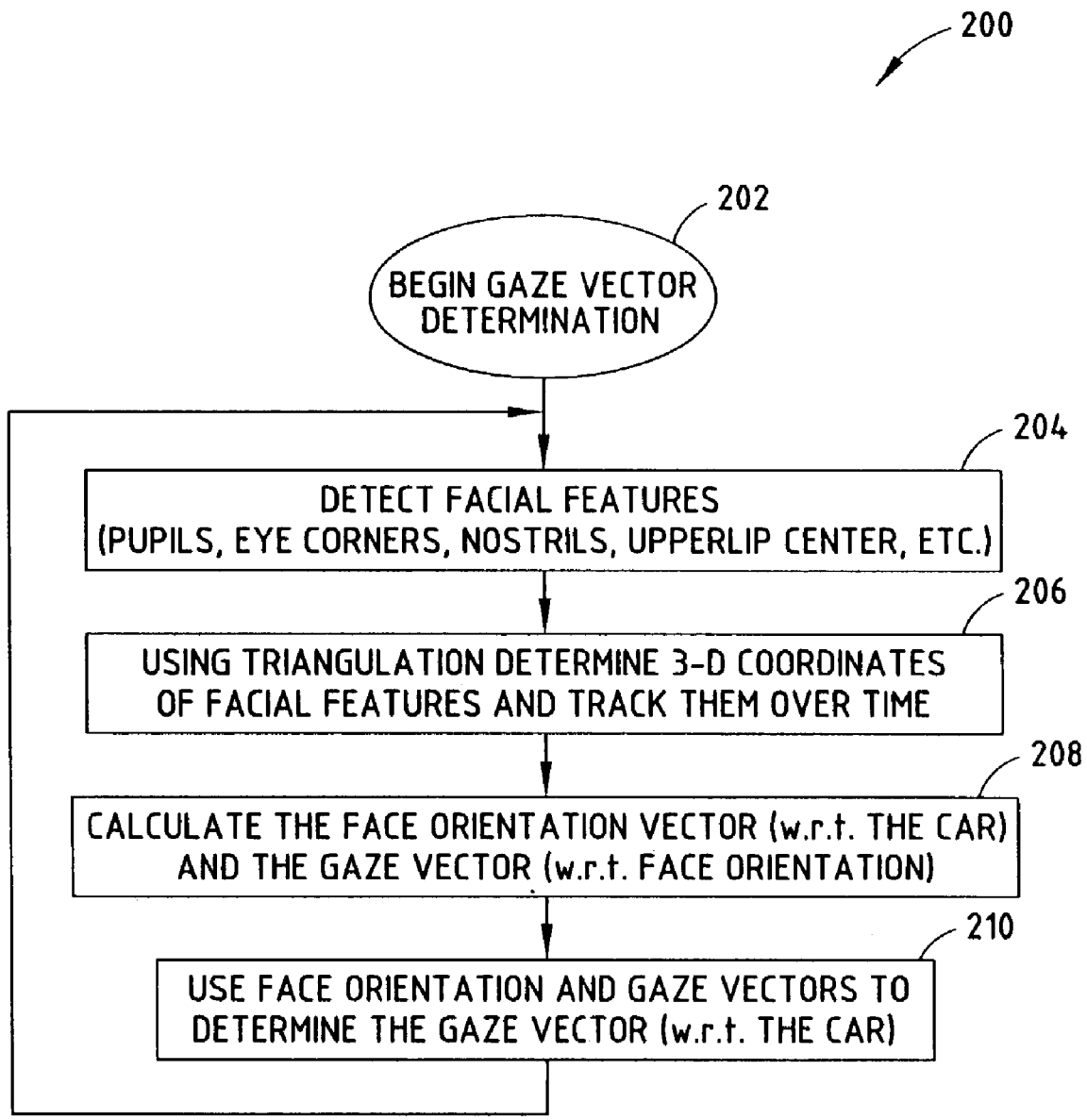
FIG. 11 is a flow diagram illustrating a routine for determining a gaze vector of the driver of the vehicle.

Referring to FIG. 11, a routine 200 is shown for determining the gaze vector $\bar{g}$ of the driver of the vehicle. The routine 200 begins at step 202 and proceeds to step 204 to detect facial features of the driver including the eye pupils, eye corners, nostrils, upper lip, and other features. Once the facial features of the head of the driver are detected, routine 200 determines the three-dimensional coordinates of the facial features of the driver's head using triangulation and tracks the facial features over time in step 206. Next, routine 200 calculates the face orientation vector of the driver's head $\bar{h}=(h_x, h_y, h_z)$ with regard to the vehicle, and further calculates the gaze vector with regard to the driver's face orientation, in step 208. Finally, in step 210, routine 200 uses the face orientation vector $\bar{h}$ and gaze vector with regard thereto to determine the eye gaze vector $\bar{g}=(g_x, g_y, g_z)$ with regard to the vehicle (car), before returning to step 204.

Figure 12:
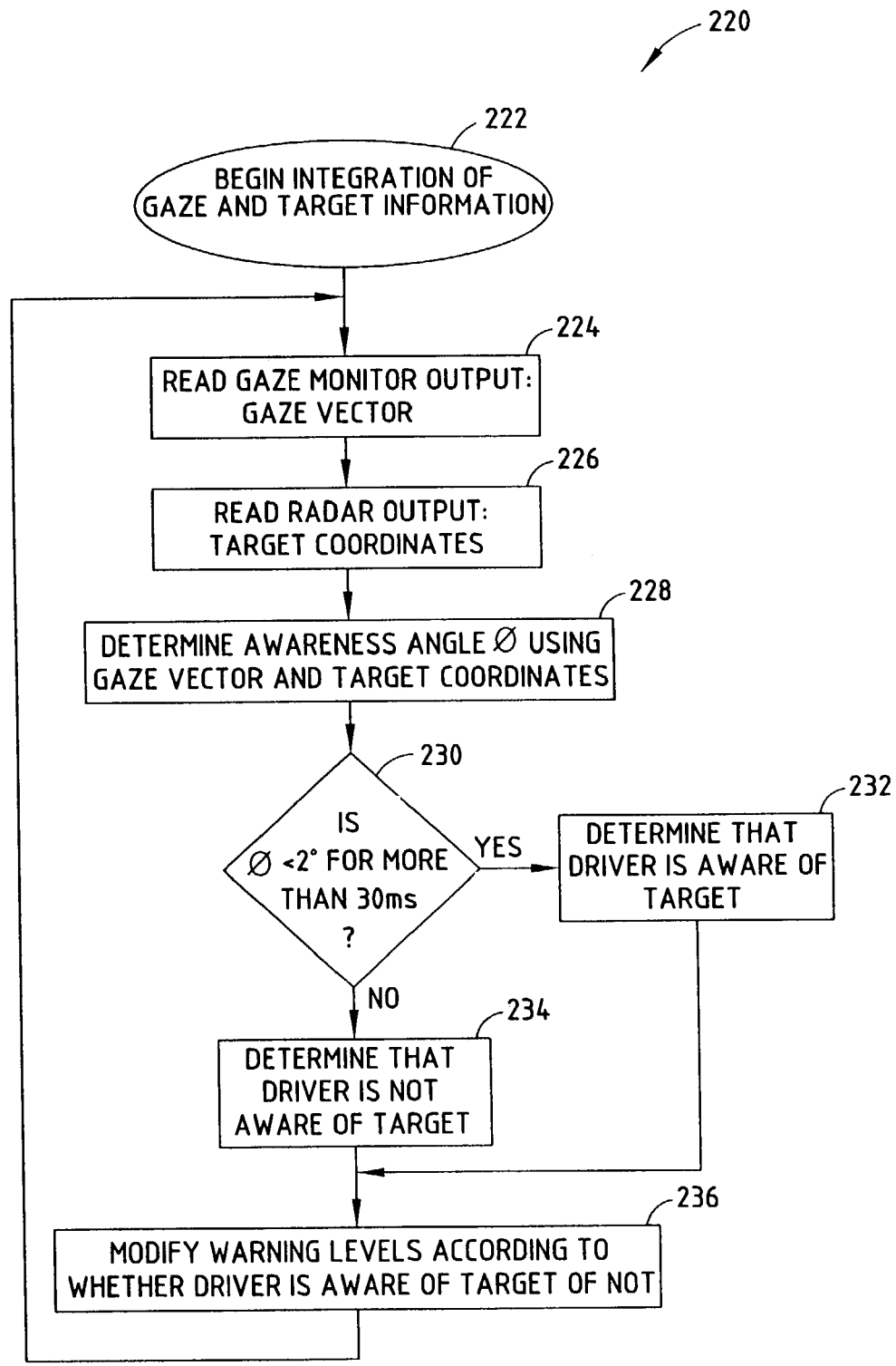
FIG. 12 is a routine integrating gaze and target information to determine driver awareness of an object and modify warning levels.

Referring to FIG. 12, a routine 220 is shown for determining a driver awareness condition and modifying warning levels based on the driver awareness condition. Routine 220 begins at step 222 and proceeds to read the eye gaze monitor output, which is the gaze vector $\bar{g}=(g_x, g_y, g_z)$, in step 224. Next, in step 226, routine 220 reads the radar output, which are the target coordinates $\bar{t}=(t_x, t_y, t_z)$. Proceeding to step 228, routine 220 determines the awareness angle φ using the gaze vector $\bar{g}$ and the target coordinates $\bar{t}$. In decision step 230, routine 220 determines if the awareness angle φ is less than about two degrees (2°) for more than a predetermined time period of thirty milliseconds (30 ms). If the awareness angle φ is less than about two degrees (2°), routine 220 determines that the driver is aware of the target in step 232. Otherwise, if the awareness angle φ is not less than about two degrees (2°) for the predetermined time period, routine 220 determines that the driver is not aware of the target in step 234. In step 236, routine 220 further modifies warning levels according to whether the driver is aware of the target or not. This may include adaptively shifting warning thresholds in a collision detection system or other warning systems.

Accordingly, the target awareness determination system of the present invention advantageously integrates the object tracking system 18 and eye gaze monitor system 38 to determine whether the driver 34 of the vehicle 10 is aware of a detected target object 16 so as to provide an increased level of security in operating the vehicle 10. The target awareness determination system advantageously improves vehicle operation for occupants and pedestrians in the vehicle 10, provides more relevant warnings given to the driver 34, minimizes the occurrence of nuisance alarms and thus driver disregard based on nuisance alarms, and better integrates existing vehicle systems.

It will be understood by those who practice the invention and those skilled in the art, that various modifications and improvements may be made to the invention without departing from the spirit of the disclosed concept. The scope of protection afforded is to be determined by the claims and by the breadth of interpretation allowed by law.

What is claimed is:

1. A target awareness determination system for determining user awareness of an object, said system comprising:
   an object monitor including an object detection sensor for sensing an object in a field of view and determining a position of the object;
   an eye gaze monitor including an imaging camera oriented to capture images of a user including an eye of the user, said eye gaze monitor determining an eye gaze vector; and
   a controller for determining awareness of the user to the object based on the detected object position and the eye gaze vector, wherein the controller further determines an awareness angle as a function of the gaze vector and the position of the object, wherein the controller determines driver awareness as a function of the awareness angle.

2. The system as defined in claim 1, wherein the user is a driver of a vehicle and the controller determines awareness of the driver of the vehicle to an object sensed by the object detection sensor located on the vehicle.

3. The system as defined in claim 1, wherein the controller determines awareness of the user to the object when the awareness angle is less than a predetermined angle.

4. The system as defined in claim 3, wherein the predetermined angle is about two degrees.

5. The system as defined in claim 1, wherein the controller determines awareness of the user to the object when the awareness angle is less than the predetermined angle for a predetermined time period.

6. The system as defined in claim 5, wherein the predetermined time period is at least 30 milliseconds.

7. The system as defined in claim 1, wherein the object detection sensor comprises a radar sensor, and the imaging camera comprises a video camera.

8. The system as defined in claim 1, wherein the controller generates an output signal for modifying a collision warning system as a function of the determination of user awareness to the object.

9. A target awareness determination system for determining vehicle driver awareness of an object, said system comprising:
   an object monitor including an object detection sensor mounted on a vehicle for sensing an object in a field of view and determining a position of the object;

an eye gaze monitor including an imaging camera mounted on the vehicle and oriented to capture images of a driver of the vehicle including an eye of the driver, said gaze monitor determining an eye gaze vector; and a controller for determining awareness of the driver of the object based on the detected object position and the eye gaze vector, wherein the controller further determines an awareness angle as a function of the gaze vector and the position of the object, wherein the controller determines driver awareness as a function of the awareness angle.

10. The system as defined in claim 9, wherein the controller determines vehicle driver awareness of the object when the awareness angle is less than a predetermined angle.

11. The system as defined in claim 10, wherein the predetermined angle is about two degrees.

12. The system as defined in claim 9, wherein the controller determines vehicle driver awareness when the awareness angle is less than the predetermined angle for a predetermined time period.

13. The system as defined in claim 12, wherein the predetermined time period is at least 30 milliseconds.

14. A method of determining user awareness of an object, said method comprising the steps of:
- sensing the presence of an object in a field of view;
- determining a position of the object within the field of view;
- monitoring eye gaze of a user;
- determining an eye gaze vector of the user; and
- determining an awareness angle as a function of the eye gaze vector and the position of the object; and
- determining the user awareness as a function of the awareness angle.

15. The method as defined in claim 14, wherein the step of determining user awareness further comprises comparing the awareness angle to a predetermined angle.

16. The method as defined in claim 15, wherein the predetermined angle is about two degrees.

17. The method as defined in claim 14, wherein the step of determining user awareness comprises comparing the awareness angle to a predetermined angle for a predetermined time period.

18. The method as defined in claim 17, wherein the predetermined time period is at least 30 milliseconds.

19. The method as defined in claim 14, wherein the method is performed on a vehicle to determine awareness of a driver of the vehicle.

20. A method of determining vehicle driver awareness of an object, said method comprising the steps of:
- sensing the presence of an object in a field of view;
- determining a position of the object within the field of view;
- monitoring eye gaze of a driver of a vehicle;
- determining an eye gaze vector of the driver of the vehicle; and
- determining an awareness angle as a function of the eye gaze vector and the position of the object; and
- determining the user awareness as a function of the awareness angle.

* * * * *